United States Patent [19]

Franck et al.

[11] 4,092,371

[45] May 30, 1978

[54] PROCESS FOR MANUFACTURING A CATALYST COMPRISING ALUMINUM OXIDE AND BORON OXIDE, THE RESULTING CATALYST AND THE USE THEREOF IN ALKYLATION REACTIONS

[75] Inventors: Jean-Pierre Franck, Bougival; Jean-François Le Page, Rueil-Malmaison, both of France

[73] Assignee: Institut Francais du Petrole, Rueil-Malmaison, France

[21] Appl. No.: 815,350

[22] Filed: Jul. 7, 1977

Related U.S. Application Data

[62] Division of Ser. No. 699,454, Jun. 24, 1976.

[30] Foreign Application Priority Data

Jun. 25, 1975 France .................................. 75 20198

[51] Int. Cl.$^2$ ................................................ C07C 3/52
[52] U.S. Cl. .............................. 260/671 C; 260/671 R;
[58] Field of Search ........... 260/671 R, 671 C, 671 B; 252/428, 430

[56] References Cited

U.S. PATENT DOCUMENTS

| 2,480,254 | 8/1949 | Mavity ................................. 252/432 |
| 2,946,778 | 7/1960 | Hammond et al. ................... 252/430 |
| 3,054,836 | 9/1962 | Hervert et al. .................. 260/671 R |
| 3,079,328 | 2/1963 | Christensen ......................... 252/432 |
| 3,096,385 | 7/1963 | McConnell et al. ................. 252/430 |
| 3,230,270 | 1/1966 | Kovack et al. .................. 260/671 R |

*Primary Examiner*—Delbert E. Gantz
*Assistant Examiner*—C. E. Spresser
*Attorney, Agent, or Firm*—Millen & White

[57] ABSTRACT

A catalyst useful for the alkylation of aromatic hydrocarbons is produced by reacting a compound of the formula $AlX_yR_{(3-y)}$, where X is halogen, R is a hydrocarbon radical and y is 1, 3/2, 2 or 3, except 3 when X is fluorine, with a carrier comprising aluminum oxide and boron oxide.

11 Claims, No Drawings

PROCESS FOR MANUFACTURING A CATALYST COMPRISING ALUMINUM OXIDE AND BORON OXIDE, THE RESULTING CATALYST AND THE USE THEREOF IN ALKYLATION REACTIONS

This is division, or application Ser. No. 699,454 filed June 24, 1976.

This invention concerns a process for manufacturing a catalyst containing alumina and boron, the resulting catalyst and its use for alkylating hydrocarbons, particularly aromatic hydrocarbons, in view of producing, for example, ethylbenzene and higher alkylaromatic hydrocarbons.

A process for alkylating aromatic hydrocarbons which is largely used on an industrial scale makes use, as catalyst, of aluminum trichloride or complexes or solutions thereof. This process, however, has a disadvantage : since complexes of aromatic hydrocarbons with aluminum chloride are formed, two additional steps are necessary, one for decomposing the complex, the other for washing carefully the aromatic hydrocarbons. In the absence of such treatments, the resulting hydrocarbons have excessive chlorine contents.

The object of the invention is to describe the manufacture and use in alkylation reactions of a solid catalyst of good stability which does not form undesirable complexes with the aromatic hydrocarbons.

The catalyst is obtained by contacting an aluminum halide or a hydrocarbyl aluminum halide with a carrier containing aluminum oxide and boron oxide. This treatment is usefully followed with heating to a temperature from 300 to 800° C. Although the basic mechanism of the operation is not known with certainty, it appears that a true reaction takes place between the aluminum halide or hydrocarbyl aluminum halide and the mixture of the boron and aluminum oxides. The presence of boron oxide appears to be essential : when by the same method, in the absence of boron oxide, there is prepared a catalyst which is used for alkylation, it is observed that this catalyst quickly loses its initial activity and that the alkylate contains a substantial amount of aluminum compound or complex.

The usual amount of boron oxide is 0.01 to 1 part by weight per part by weight of aluminum oxide. Additional refractory oxides may be present, for example, acidic oxides such as silica, although this is not preferred.

The preferred aluminum oxide is in a form having a substantial specific surface, preferably at least 5 m$^2$ per gram, either when admixing the ingredients or after calcination at 300° – 800° C, so that the final catalyst has itself a substantial specific surface, usefully at least 5 m$^2$/g and preferably 50 - 500 m$^2$/g.

Boron oxide may be supplied as such or preferably as a compound convertible to boron oxide by heating. Any boric acid is used.

The mixture of aluminum oxide with boron oxide may be effected in any known manner, for example by mechanical mixing of the powders, either dry or in the presence of water, or preferably by impregnating alumina with an aqueous solution of a boric acid. Instead of oxides or acids, compounds convertible to oxides by heating, such as nitrates, can be used. Thereafter the mixture is dried, if necessary, for example by heating to 100° – 500– C.

The mixture of the aluminum and boron oxides is preferably contacted with an aluminum halide or hydrocarbyl aluminum halide in the absence of water and oxygen, by using dry oxides to avoid any unnecessary and even detrimental secondary reaction of hydrolysis of the aluminum halide or the hydrocarbyl aluminum halide.

The aluminum halide or the hydrocarbyl aluminum halide may be reacted with the mixture of the aluminum and boron oxides at room temperature or at any temperature compatible with the stability of the reactants, usually between −20° and + 250° C or more.

The amount of aluminum halide or hydrocarbyl aluminum halide, calculated as halogen, to be introduced into the catalyst is usually 0.5 – 20 %, preferably 4 – 12 % by weight of the alumina.

Since the aluminum halide or the hydrocarbyl aluminum halide is relatively easily and practically completely retained by the carrier, it is normally unnecessary to use an excess of this halide.

The hydrocarbyl aluminum halide is preferably used as a solution in a non-reactive solvent, for example, a hydrocarbon preferably containing 5 - 20 carbon atoms per molecule or a halogenated hydrocarbon.

The aluminum or hydrocarbyl aluminum halides are of the general formula $AlX_yR_{(3-y)}$ where y is 1, 3/2, 2 or 3 and X is halogen, preferably chlorine, except the case where simultaneously X is fluorine and y is 3; R is a monovalent hydrocarbon radical containing, for example, 1 to 20 carbon atoms. Examples are: diethylaluminum chloride, dodecyl aluminum dichloride, diisobutyl aluminum chloride, diethyl aluminum fluoride, benzylaluminum dichloride, phenylaluminum dichloride, cyclohexylaluminum dichloride or ethylaluminum sesquichloride.

The aluminum trihalide may be, for example, a trichloride or tribromide, for example, aluminum trichloride or aluminum tribromide. This compound may be supplied to the catalyst by impregnation or sublimation; when operating with Al Cl$_3$ by sublimation, the temperature is about 185° to 400° C. On the contrary, when operating by impregnation, any temperature compatible with an impregnation liquid phase may be used. Aluminum trifluoride does not result in an active catalyst.

When introducing the halide into the carrier, it is operated in neutral or reducing atmosphere, for example, nitrogen, hydrogen, methane, at ordinary pressure or under any other pressure.

After introduction of the aluminum or hydrocarbyl aluminum halide, the material may be heated to 300°–800° C, preferably 400° – 600° C. This treatment takes usually from 10 minutes to 24 hours, these values being not limitative. In fact, at a fairly high temperature, the treatment is substantially shorter.

The alkylation reaction is carried out with at least one aromatic hydrocarbon and at least one alkylation reactant. The aromatic hydrocarbon may be mono- or polycyclic, for example : benzene, toluene, ethylbenzene, cumene, naphthalene or diphenyle. The alkylation reactant is preferably an olefin having 2 to 16 carbon atoms, for example: ethylene, isobutylene, propylene trimer or tetramer; certain chlorinated paraffins may also be used.

The molar ratio of the alkylation agent to the aromatic hydrocarbon is usually from 0.1 : 1 to 1 : 1, preferably 0.25 : 1 to 0.5 : 1. When starting with ethylene, the latter may be pure or diluted with an inert gas, for example methane, ethane, propane, nitrogen or hydrogen.

The alkylation temperature is usefully from 100° to 300° C, preferably from 125° to 200° C. The pressure must be sufficient to maintain the aromatic hydrocarbon in the liquid phase and ensure a sufficient amount of the olefin, as defined above. When alkylating benzene with ethylene, the pressure is usually from 5 to 50 atm, preferably from 10 to 30 atm.

A dispersed catalyst may be used, but it is preferred to circulate the reactants through the catalyst in fixed bed. The feed rate (VVH) is, for example, 0.25 to 20, preferably 1 to 5 (volumes of aromatic hydrocarbon per volume of catalyst per hour).

The reaction being strongly exothermic, the temperature will be maintained at an acceptable value by removing heat in any known manner, for example, cooling of the reactor walls, vaporization of a portion of the liquid flow, recycling of a portion of the reactor effluent after cooling thereof.

A halide promoter is preferably added to the reactants, either continuously or periodically, for example, a hydrogen halide such as hydrochloric acid or hydrofluoric acid, or a hydrocarbyl mono- or poly-halide, for example methyl chloride, ethyl chloride, tertarybutyl chloride, chloroform, carbon tetrachloride or dichlorodifluoromethane. This promoter is usually present in an amount of 10 - 10,000 ppm b.w. with respect to the aromatic hydrocarbon to be alkylated. It is advantageous to recycle the unconverted reactants and the gaseous effluent from the reactor containing halogenated compounds, so that the halogen consumption may be very low. The products such as the polyalkylbenzenes whose alkylation degree is too high may be recycled when producing a monoalkylbenzene.

The ethylbenzene fraction which may be obtained by distillation of the effluent from the present process, when applied to benzene and ethylene, is practically free from halogen. It is thus unnecessary to subject it to the conventional treatments of decomposition of the complexes and thorough washing.

EXAMPLE 1 (comparison example without boron oxide).

100 g of alumina having a specific surface of 300 m$^2$/g and a pore volume of 0.5 cc/g is roasted in the air for 1 hour at 400° C. It is then arranged in a tubular reactor of stainless steel.

The reactor is then scavenged with a dry hydrogen stream supplied at a rate of 50 liters of hydrogen per liter of catalyst and per hour, at 400° C and a pressure of 5 bars absolute. The temperature is then decreased to 150° C and the pressure raised to 20 bars absolute; 1200 cc of a solution of 0.12 mole Al$_2$Cl$_3$ (C$_2$H$_5$)$_3$ per liter of normal hexane is then injected with a pump at a rate of 100 cc per hour; the effluent from the reactor is then recycled.

After a 10 hours circulation, the pump is stopped, the solvent is removed and the solid is dried in hydrogen in the following conditions:
pressure: 20 bars absolute;
temperature: 400° C;
hydrogen feed rate: 50 liters per liter of solid per hour;
time: 2 hours.

An analysis of the halogenated solid shows that the latter contains 7.4 % b.w. of chlorine.

The resulting catalystis then used for alkylating benzene with ethylene, the catalyst being arranged as a fixed bed in the tubular reactor.

The operating conditions for the alkylation are the following: pressure: 20 bars absolute; temperature: 150° C; molar ratio benzene/ethylene: 4/1; benzene space velocity (VVH): 2 liters per liter of catalyst per hour; hydrogen: 100 liters per liter of catalyst per hour; water content of benzene <10 ppm by weight; chlorine promoter: C$_2$H$_5$Cl 0.35 % b.w./benzene.

The reaction products are analyzed by vapor phase chromatography; their composition is given in the following table:

| TIME IN HOURS PRODUCTS % b. w. | 10 | 15 | 20 | 30 | 50 |
|---|---|---|---|---|---|
| Benzene | 77.3 | 76.8 | 76 | 82.0 | 85.0 |
| Ethylbenzene | 20.3 | 20.1 | 19.8 | 15.1 | 13.5 |
| Diethylbenzene | 2.4 | 3.1 | 4.1 | 2.8 | 1.5 |
| Polyethylbenzene | Traces | Traces | 0.1 | 0.1 | Traces |

The analysis of the products obtained after 15 hours and 50 hours shows that they contain respectively, after washing with 0.1 normal sodium hydroxide solution and neutralization:
chlorine: 105 and 150 ppm
aluminum: 750 and 1100 ppm In this experiment, the reaction products are strongly coloured in brown-red, which shows the presence of complexes of the AlCl$_3$-aromatics type.

EXAMPLE 2

100 g of an alumina/boron oxide carrier containing 90% by mole alumina and 10% by mole boron oxide, obtained by comixing, extrusion and calcination of a mixture of alumina hydrate and boric acid, is arranged in fixed bed in the tubular reactor used above.

The solid is roasted at 500° C and the reactor scavenged with a stream of dry hydrogen as described in example 1. 600 cc of a solution of 100 millimoles Al$_2$Cl$_3$ (C$_2$H$_5$)$_3$ in normal hexane is injected at a rate of 100 cc per hour, while recycling the reactor effluent.

After 10 hours circulation, the solvent is discharged and the solid is dried as described in example 1.

An analysis of the resulting catalyst shows that it contains 7.2% b.w. of chlorine.

The resulting catalyst is then used for alkylating benzene with ethylene in the same conditions as in example 1.

The reaction products are analyzed by chromatography in vapor phase; they have the composition given in the following table:

| TIME IN HOURS PRODUCTS % b.w. | 15 | 50 | 100 | 200 | 500 |
|---|---|---|---|---|---|
| Benzene | 72.90 | 73.0 | 72.9 | 73.5 | 73.6 |
| Ethylbenzene | 24.49 | 24.5 | 24.6 | 24.0 | 24.0 |
| Diethylbenzene | 2.60 | 2.5 | 2.5 | 2.5 | 2.4 |
| Polyethylbenzenes | 0.01 | Traces | Traces | Traces | Traces |

All along this experiment, the products remain perfectly clear and uncolored. The analysis of the products obtained respectively after 15 hours, 50 hours and 500 hours, effected by washing with a 0.1 N sodium hydroxide solution and neutralization, shows that the latter contain less than 10 ppm of chlorine (parts per million) and less than 1 ppm of aluminum.

EXAMPLE 3

100 g of a mixed oxide is obtained by impregnating alumina of large surface with an aqueous solution of boric acid containing 25% b.w. of boric acid with respect to the amount of alumina and then calcining in dry air at 500° C for 2 hours; it is then introduced into the above tubular reactor.

The reactor is scavenged with a stream of dry hydrogen as described in example 1. 800 cc of a solution containing 0.15 mole of $AlCl_2C_2H_5$ per liter of normal heptane is then injected at 150° C under an absolute pressure of 20 bars, at a rate of 200 cc per hour with recycling of the reactor effluent.

After a 5 hour circulation, the pump is stopped, the solvent is discharged and the solid is dried in hydrogen under the following conditions: pressure: 20 bars absolute; temperature: 150° C; hydrogen feed rate: 20 liters per liter of carrier per hour: time: 3 hours.

An analysis of the resulting catalyst shows that the latter contains 5.6% b.w. of chlorine.

This catalyst is used in a reaction with benzene containing 0.1 % b.w. of ethyl chloride and a gas of high olefin content recovered from the high pressure separator of a steam-cracking unit. The gas contains 20% by mole of ethylene and 8% by mole of propylene; the operating conditions are:

pressure: 40 bars absolute; temperature: 150° C; molar ratio benzene/olefines: 6.5/1; water content of benzene <10 ppm by weight; benzene space velocity (VVH): 2 liters per liter of catalyst per hour.

After a 30 hour run, the analysis of the product gives the following composition by weight:

| benzene | 84.7 % | |
|---|---|---|
| ethylbenzene | 8.5 % | |
| isopropylbenzene | 6.1 % | |
| polyalkylbenzenes | 0.7 % | |
| chlorine | <10 ppm | after washing with a sodium hydroxide solution and neutralization - |
| aluminum | <1 ppm | |

EXAMPLE 4

After a 50 hour run in the conditions of example 3, the feed charge of example 1 is passed in the following conditions: pressure: 35 bars absolute; temperature: 150° C; molar ratio benzene/ethylbenzene: 4/1; benzene space velocity (VVH): 2; dry nitrogen: 150 liters per liter of catalyst per hour; ethyl chloride: 0.08% b.w./benzene; water content of benzene <10 ppm b.w.

After a 100 hour run in the above conditions, the resulting product has a density of 0.875 at 15° C; it is distilled into 3 fractions without prior washing and neutralization.

| | TEMPERATURE ° C | % BY WEIGHT | $d_4^{15}$ |
|---|---|---|---|
| Fraction No. 1 | <110 | 70.78 | 0.880 |
| Fraction No. 2 | 110 – 137 | 23.16 | 0.868 |
| Fraction No. 3 | >137 | 5.92 | 0.874 |
| Loss | | 0.14 | |

Fraction No. 2 consists of practically pure ethylbenzene ($d_4^{15}$ ethylbenzene = 0.8672 according to Handbook of Chemistry and Physics); it contains less than 1 ppm b.w. of chlorine and less than 1 ppm b.w. of aluminum.

EXAMPLE 5

100 g of a mixed oxide alumina/boron oxide containing 75% b.w. of $Al_2O_3$ and 25% b.w. of $B_2O_3$ is placed in the above mentioned tubular reactor. The temperature of the reactor is raised to 400° C while passing for 2 hours an air stream at a feed rate of 600 liters per liter of solid per hour.

The temperature is decreased to 250° C and the air is replaced with nitrogen which is previously passed in contact with aluminum chloride at 200° C: aluminum chloride sublimates and, after scavenging with nitrogen, deposes on the alumina/boron oxide carrier.

After 1 hour of treatment, $AlCl_3$ sublimation is stopped and the temperature of the catalyst bed is raised to 400° C while maintaining a nitrogen stream in order to eliminate $AlCl_3$ in excess.

The analysis of the resulting catalyst shows that the latter contains 8.1% b.w. of chlorine. It is then used to alkylate benzene with ethylene under the following conditions:

pressure: 25 bars absolute;
temperature: 180° C;
molar ratio benzene/ ethylene: 4;
benzene space velocity (VVH): 2 liters per liter of catalyst per hour;
water content of benzene <10 ppm b.w.;
chlorinated promoter: $C_2H_5Cl$ (0.05% b.w./benzene);
methane: 50 liters/liter of catalyst per hour.

After 30 hours run, the chromatograhic analysis of the reaction product shows that the latter has the following composition by weight:
benzene: 77.1%
ethylbenzene: 19.5%
diethylbenzene: 3.3%
polyalkylbenzene: 0.1%
chlorine content: <10 ppm
aluminum content: <1 ppm

EXAMPLE 6

100 g of catalyst is prepared, as in example 2. This catalyst is then used for alkylating benzene with a mixture of hydrocarbons having 11 to 13 carbon atoms and whose composition by weight is:
paraffins: 89%
olefins: 10.8%
aromatics: 0.2%

The alkylation is effected in the following operating conditions:
pressure: 6 bars absolute
temperature: 120° C
molar ratio benzene/olefins: 4/1
benzene space velocity: 1 liter/liter of catalyst per hour
water content of the reactants <10 ppm b.w.
chlorinated promoter: $(CH_3)_3 CCl$: 0.15% b.w./benzene.

After a 50 hour run, a sample of product is fractionated to a benzene cut, a $C_{11}$-$C_{13}$ hydrocarbon cut and the alkylate.

The analysis of the products shows that the $C_{11}$-$C_{13}$ hydrocarbon cut has the following composition by weight:
paraffins: 99.4%
olefins: 0.2%
aromatics: 0.4%

The alkylate has the following composition:
monoalkylbenzenes: 97%
dialkylbenzenes: 3%.

What we claim is:

1. In the alkylation of an aromatic hydrocarbon with an olefin at about 100–300° C. and under sufficient pressure to maintain the aromatic hydrocarbon in the liquid phase and wherein the proportion of the olefin to the aromatic hydrocarbon is about 0.1 : 1 to 1 : 1, in contact with a catalyst, the improvement wherein said catalyst is that catalyst produced by reacting an aluminum compound of the formula $AlX_yR(3-y)$ where X is halogen, R is a hydrocarbon radical and $y$ is 1, 3/2, or 2, with a carrier consisting essentially of a mixture of aluminum oxide and boron oxide in proportions by weight of 1 : 0.01 to 1 : 1, respectively, and wherein the compound of formula $AlX_yR_{(3-y)}$ is used in a sufficient amount to introduce 0.5 – 20% by weight of halogen into the catalyst.

2. An alkylation process according to claim 1, wherein prior to use, the catalyst is heated to 300°–800° C.

3. An alkylation process according to claim 1, wherein the mixture of aluminum oxide and boron oxide for producing the catalyst results from impregnating alumina with an aqueous solution of boric acid, and the resultant mixture is heated to 100°–500° C.

4. An alkylation process according to claim 1, wherein the aluminum oxide has a specific surface of at least 5 square meters per gram.

5. An alkylation process according to claim 1, wherein a halogenated promoter is present in an amount of 10 to 10,000 ppm b.w. with respect to the aromatic hydrocarbon to be alkylated.

6. An alkylation process according to claim 1, wherein benzene is alkylated with ethylene.

7. An alkylation process according to claim 1, wherein benzene is alkylated with a mixture of hydrocarbons having 11 to 13 carbons atoms.

8. An alkylation process according to claim 1, wherein X is chlorine in the compound of the formula $AlX_yR_{(3-y)}$, and said compound is used in a sufficient amount to introduce 4-12% b.w. of chlorine into the catalyst.

9. An alkylation process according to claim 1, wherein said reacting is carried out at a temperature of −20° to +250° C.

10. An alkylation process according to claim 2, wherein said heating is carried out at 400° – 600° C.

11. An alkylation process according to claim 1, wherein the catalyst is present in fixed bed and the feed rate is 0.25 to 20 volumes of liquid aromatic hydrocarbon per volume of catalyst per hour.

* * * * *